United States Patent [19]

Gopinathan et al.

[11] Patent Number: 5,856,575

[45] Date of Patent: Jan. 5, 1999

[54] PROCESS FOR THE PREPARATION OF N-ACETYL AMINOPHENOLS

[75] Inventors: Sarada Gopinathan; Changaramponnath Gopinathan; Joseph Kuruvilla; Sanjeevani Amrit Pardhy; Paul Ratnasamy, all of Pune, India

[73] Assignee: Council of Scientific Industrial Research, New Dehli, India

[21] Appl. No.: 787,080

[22] Filed: Jan. 22, 1997

[51] Int. Cl.⁶ .................................................. C07C 233/05
[52] U.S. Cl. ........................ 564/223; 564/216; 564/217; 564/218
[58] Field of Search ..................... 564/223, 218, 564/216, 217

[56] References Cited

U.S. PATENT DOCUMENTS 3,702,882  11/1972  Rettew et al. .
5,221,769   6/1993  Akeida et al. ..................... 564/223
5,387,702   2/1995  Changaramponnath et al. .

FOREIGN PATENT DOCUMENTS 0 265 017 B1  4/1988  European Pat. Off. .
0 266 825 B1  5/1988  European Pat. Off. .
0 321 020 B1  6/1989  European Pat. Off. .
    164459   3/1989  India .

*Primary Examiner*—Shailendra Kumar
*Attorney, Agent, or Firm*—Akin, Gump, Strauss, Hauer & Feld, LLP

[57] ABSTRACT

This invention provides a process for the manufacture of N-acetyl amino phenol, which process comprises reacting an appropriate phenol and an amide in the presence of a heteropoly acid or its alkali metal salt catalyst.

19 Claims, No Drawings

PROCESS FOR THE PREPARATION OF N-ACETYL AMINOPHENOLS

FIELD OF THE INVENTION

This invention deals with a process for the manufacture of N-acetyl aminophenols.

BACKGROUND AND PRIOR ART REFERENCES OF THE INVENTION

The reaction between para aminophenol and acetic anhydride is the most common one known in the prior art for making N-acetyl aminophenol. Para aminophenol, in turn, is manufactured either by the reduction of para nitrophenol or para nitrosophenol. Hydrogen reduction of nitrobenzene under acidic conditions is another commercial method for making para aminophenol. Another process known in the art for the manufacture of N-acetyl para aminophenol employs the Beckmann rearrangement of para hydroxyacetophenone oxime; para hydroxyacetophenone is commercially manufactured by the Fries rearrangement of phenyl acetate in presence of aluminium chloride or hydrogen fluoride. European Patent Application 321020 claims the use of molecular sieves to catalyze the reaction between phenols and amides to give N-acyl anilines. Manufacture of N-acetyl para aminophenol either from para aminophenol or by employing the Fries rearrangement, causes environmental pollution because these routes use toxic aluminium chloride or hydrogen fluoride.

SUMMARY OF THE INVENTION

To overcome the above problems, the applicants have now provided a simple, economic and eco-friendly process for the production of N-acetyl aminophenol which will reduce environmental pollution to the minimum. This process involves reacting a phenol with an amide in the presence of a solid catalyst composite material containing a heteropoly acid.

DETAILED DESCRIPTION OF THE INVENTION

The main finding of the present invention is that N-acetyl aminophenols can be manufactured by an improved process which comprises of reacting a phenol with an amide in the presence of a solid catalyst composite material containing a heteropoly acid at a temperature in the range 100° to 400° C. and separating the N-acetamino derivative from the products of the reaction. The applicants have found that heteropoly acids or their salts are most efficient catalysts to produce the N-acetylaminophenols from the reaction between the amide and the phenol. The solid heteropoly acids or their salts may be used as such or in the composite supported form on porous materials like silica, thoria or silica alumina. The phenol may be a polyhydroxy phenol such as catechol, resorcinol, hydroquinone, pyrogallol, phloroglucinol or polyhydroxy naphthols, and the amide may be selected from acetamide, propionamide or benzamide or it may be derived from a lower fatty acid such as acetic or propionic or may be generated "in situ" from the ammonium salt of the fatty acid. The amide can be added to the reaction mixture either as such or generated "in situ" for example, by dehydration of the ammonium salt:

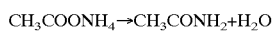

In its broadest aspects, the present invention involves the use of a solid acid catalyst for the selective condensation of one of the hydroxyl groups of a polyhydroxy phenol such as catechol, resorcinol, hydroquinone, pyrogallol, phloroglucinol or polyhydroxy naphthols. The invention is best illustrated by the formation of N-acetyl para aminophenol from hydroquinone and acetamide though it is not restricted to the preparation of N-acetyl para amino phenol only.

Accordingly, the present invention provides an improved process for the preparation of N-acetyl aminophenol which comprises reacting an appropriate phenol and an amide in the presence of a heteropoly acid or its alkali metal salts at a temperature in the range of 100° to 400° C. and isolating the corresponding N-acetyl aminophenol from the reaction mixture by conventional methods of solvent extraction and crystallization. Exemplary reactions are shown here below:

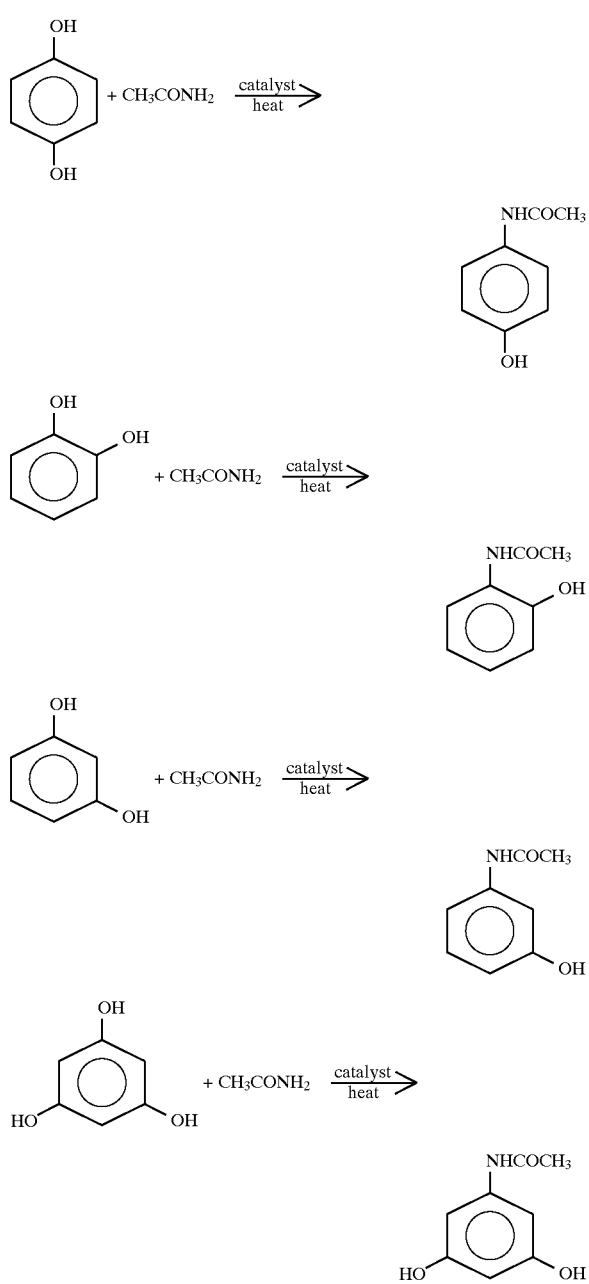

Examples of heteropoly acids are silicotungstic acid, phosphotungstic acid, phosphomolybdic acid and vanadotungstic acid. They have a common crystal structure comprising of a central tetrahedron constituted of, for example, $SiO_4$ or $PO_4$ units surrounded by twelve $MO_6$ octahedra wherein M=Mo, or W.

In an embodiment of the present invention, the heteropoly acid is combined with a binder to constitute the final catalyst composite material. Such an operation imparts to the catalyst desirable properties such as good mechanical strength, large and active surface, ease of handling, lower and optimal utilization of the heteropoly acid. Examples of such binders are silica, alumina, thoria, silica-alumina, clays, kieselguhr. A particularly preferred binder is silica. Indian Patent 164459 describes in more detail the preparation of the heteropoly acid based solid catalyst composite material used in the process of the present invention.

In another embodiment of the process of this invention, the catalyst composite material is prepared by impregnating an aqueous solution of a heteropoly acid on an inert binder to obtain a uniform impregnation of the catalytically active material, the heteropoly acid, on the high surface of the inert binder followed by removal of water at a temperature not exceeding 400° C. Preferably, the space hourly velocity of the feed is maintained in the range of 0.1 to 10 g/g of the catalyst.

In another embodiment of the present invention the inert binder can be in any conventional physical form like granules, extrudates, tablets or rings, known to those skilled in the art.

In a preferred embodiment of the present invention hydroquinone is reaction with acetamide at temperatures 100°–400° C. in presence of a solid catalyst comprising of a heteropoly acid either alone or combined with an inert support in a steel tube or in a flow reactor. The ratio of hydroquinone to acetamide could be varied from 1:1 to 1:3 moles (preferably 1:1.2), and the weight hourly space velocity of the feed, comprising of hydroquinone and acetamide, between 0.1 to 10 g/g of catalyst (preferably 0.3 to 2). The concentration of the heteropoly acid in the catalyst composite could be varied between 5 to 80% by wt., preferably between 10 and 30% by wt. N-Acetyl para amino phenol could be separated from the products of the reaction by solvent extraction and crystallization, known in the prior art.

The preparation of the catalyst composite material of the present invention is described in detail in the Indian Patent 164459. Still, for better understanding of the present invention the preparation of such catalyst material is further described with reference to the following examples. These are for the purposes of illustration only and are not to be construed as limitations.

EXAMPLE 1

Preparation of the Catalyst

Silica gel, mesh size 5–15, was used as the silica support. Phosphotungstic acid (10 g) was dissolved in water (25 ml) and the solution was mixed with silica gel (100 g). The slurry was stirred to get a uniform impregnation, dried in air at 200°–250° C. for one hr., then at 400° C. for three hrs, and finally cooled to room temperature in a desiccator. This catalyst was used for the reaction between hydroquinone and acetamide.

EXAMPLE 2

Preparation of N-acetyl Para Aminophenol from Hydroquinone and Acetamide

An intimate mixture of hydroquinone (5.5 g), acetamide (3.5 g) and phosphotungstic acid (0.3 g) was placed in a well stoppered stainless steel tube from which air has been displaced with nitrogen. The tube was kept in a temperature controlled oven at 280°–300° C. for 1.5 hrs. The tube was then removed from the oven, cooled, opened, contents extracted with ethyl acetate, crystallized and products analyzed by gas chromatography. Pure standard substances were used for calibration. The products were also analyzed and identified by GC-mass spectroscopy techniques. The conversion of hydroquinone was 95% by wt. and selectivity to N-acetyl para aminophenol was 86%. Pure N-acetyl para aminophenol could be isolated from the products by column chromatography using alumina.

EXAMPLE 3

Example 2 was repeated using other catalysts such as silicotungstic acid, phosphomolybdic acid, vanadotungstic acid or their alkali metal salts such as ammonium, potassium and cesium, 0.3 to 1 g each time. The conversion and selectivity of hydroquinone were in the range 80–95% and 75–85% respectively.

Above experiments were carried out using the catalyst (3 g) comprising of the heteropoly acid (10%) supported on silica gel prepared as in Example 1. Separation of catalyst from the reaction products was by filtration; conversion and selectivity were found to be the same as in the case of using free heteropoly acids.

EXAMPLE 4

Experiments were carried out as in Examples 2 and 3 using the catalyst (3 g) comprising of the heteropoly acid (10%) supported on silica gel prepared as in Example 1. Separation of catalysts from the reaction products were achieved by filtration and we noticed that the hydroquinone conversion was 80–95% and selectivity to N-acetyl para aminophenol was 75–85%.

EXAMPLE 5

Preparation of N-acetyl Para Aminophenol from Hydroquinone and Acetamide in a Flow Reactor The experiment was carried out in a downward flow glass reactor of diameter 2 cm and of sufficient length which was kept in a furnace of length 32 cm. In the middle of the reactor was kept the catalyst (11 g) made as in Example 1, and heated to 280°–300° C. in a current of air. A solution of hydroquinone (11 g) and acetamide (7.2 g) in acetone (100 ml) was fed at a rate of 8 ml/hr. The products formed were condensed in a specially designed heated receiver, weighed and analyzed by gas chromatography. The conversion and selectivity of hydroquinone to N-acetyl para aminophenol were found to be 80–95% by wt. and 75–85% respectively.

EXAMPLE 6

An intimate mixture of hydroquinone (5.5 g), ammonium acetate (8 g) and cesium salt of silicotungstic acid (0.4 g) was heated to 300° C. in a closed stainless steel tube in a temperature controlled furnace for 1 hr, and product isolated by solvent extraction with ethyl acetate, crystallized, analyzed and characterized as in Example 2. The conversion of hydroquinone was 88% by wt. and selectivity to N-acetyl para aminophenol 77%.

EXAMPLE 7

Preparation of N-acetyl Meta Aminophenol

An intimate mixture of resorcinol (5.5 g), acetamide (4 g) and phosphotungstic acid (0.25 g) was heated to 300° C. in a sealed glass ampule and products processed and analyzed as in Example 2. The conversion of resorcinol to N-acetyl meta aminophenol was 62% by wt. and selectivity 88%.

EXAMPLE 8

Preparation of N-acetyl Ortho Aminophenol

An intimate mixture of catechol (5.5 g), ammonium acetate (5.9 g) and the catalyst described in Example 1 (11.5 g) was heated to 300° C. for 2 hrs. in a sealed glass tube, and products processed and analyzed as in Example 2. The conversion and selectivity of catechol to N-acetyl ortho aminophenol were found to be 55% by wt. and 90% respectively.

We claim:

1. A process for the manufacture of N-acetyl amino phenol, which process comprises reacting a phenol and an amide in the presence of a heteropoly acid, or alkali metal salt thereof, catalyst at a temperature in the range of 100°–400° C. and isolating the N-acetyl aminophenol formed from the reaction.

2. A process as claimed in claim 1 wherein the isolation of N-acetyl aminophenol is by solvent extraction followed by crystallization.

3. A process as claimed in claim 1 wherein the heteropoly acid or salt thereof is supported on a material selected from the group consisting of silica, alumina, silica-alumina, thoria, clay and kieselguhr.

4. A process as claimed in claim 1 wherein the heteropoly acid is silicotungstic, phosphotungstic, phosphomolybdic or vanadotungstic acid.

5. A process as claimed in claim 1 wherein the phenol is selected from the group consisting of hydroquinone, catechol, resorcinol, pyrogallol, hydroxyquinol, phloroglucinol and a polyhydroxy naphthol.

6. A process as claimed in claim 1 wherein the amide is selected from the group consisting of acetamide, propionamide and benzamide.

7. A process as claimed in claim 1 wherein the reaction is carried out in the presence of acetone.

8. A process as claimed in claim 1 wherein the amide is derived from a lower fatty acid selected from the group consisting of acetic acid and propionic acid.

9. A process as claimed in claim 1 wherein the amide is generated in situ from ammonium salt of a lower fatty acid.

10. A process as claimed in claim 1 wherein the ratio of phenol to amide ranges from 1:1 to 1:3 moles.

11. A process as claimed in claim 1 wherein the space hourly velocity of the feed is in the range of 0.1 to 10 g/g of the catalyst.

12. A process as claimed in claim 1 wherein the concentration of the catalyst is in the range of 10–30% by weight.

13. The process of claim 10 wherein the ratio of phenol to amide is about 1:1.2.

14. A process for the preparation of N-acetyl amino phenol comprising reacting a polyhydroxy phenol and an amide selected from the group consisting of acetamide, propionamide, benzamide and a lower fatty acid amide, in the presence of a heteropoly acid or alkali metal salt thereof.

15. The process of claim 14 wherein the heteropolyacid or alkali metal salt thereof is in combination with a binder forming a composite catalyst material.

16. The process of claim 15 wherein the heteropolyacid or metal salt thereof is present in the composite catalyst material at about 5–80% by weight.

17. The process of claim 15 wherein the heteropolyacid or metal salt thereof is present in the composite catalyst material at about 10–30% by weight.

18. The process of claim 15 where the heteropolyacid is phosphotungstic acid.

19. A process for the preparation of N-acetyl para amino phenol comprising reacting hydroquinone and acetamide in the presence of a heteropoly acid or alkali metal salt thereof.

* * * * *